United States Patent [19]

Blair et al.

[11] Patent Number: 4,533,325

[45] Date of Patent: Aug. 6, 1985

[54] METHOD AND APPARATUS TO PRODUCE ARTIFICIAL TEETH FOR DENTURES

[75] Inventors: John J. Blair; Frank P. Fonvielle, both of York; Richard A. Smith, New Freedom; Barry D. Dehoff, York; Roger C. Shue, Red Lion, all of Pa.

[73] Assignee: Dentsply Research & Development Corp., Milford, Del.

[21] Appl. No.: 510,405

[22] Filed: Jul. 1, 1983

[51] Int. Cl.³ .............................................. A61C 13/22
[52] U.S. Cl. .................................................... 433/171
[58] Field of Search ............... 433/171, 167, 191, 196, 433/197, 199, 202, 212, 213, 214

[56] References Cited

U.S. PATENT DOCUMENTS

| | | | |
|---|---|---|---|
| 1,303,223 | 5/1919 | Wall | 433/196 |
| 1,547,643 | 7/1925 | Clapp | 264/20 |
| 1,814,717 | 7/1931 | Maizner | 433/213 |
| 1,907,923 | 5/1933 | Willis | 433/72 |
| 2,171,759 | 9/1939 | Meyer | 433/213 |
| 2,539,882 | 1/1951 | Zilinski | 433/171 |
| 2,768,440 | 10/1956 | Elliott | 433/171 |
| 4,099,329 | 7/1978 | Hawthorne | 433/199 |
| 4,189,837 | 2/1980 | Stele | 433/57 |

FOREIGN PATENT DOCUMENTS 508921 10/1930 Fed. Rep. of Germany .
295768 8/1928 United Kingdom .

Primary Examiner—John J. Wilson
Attorney, Agent, or Firm—C. Hercus Just; Edward J. Hanson, Jr.

[57] ABSTRACT

This invention pertains to a method and apparatus to fabricate economical full arch unitary upper and lower sets of artificial teeth for use in preparing dentures for edentulous dental patients and attaching said sets of teeth to denture base material by a process developed for the purpose of utilizing these sets of teeth and converting them into finished upper and lower dentures by the use of a specialized apparatus. The process and apparatus, per se, are the subject of another related application and eliminates the conventional procedure of mounting individual artificial teeth in the normal process of fabricating dentures.

4 Claims, 45 Drawing Figures

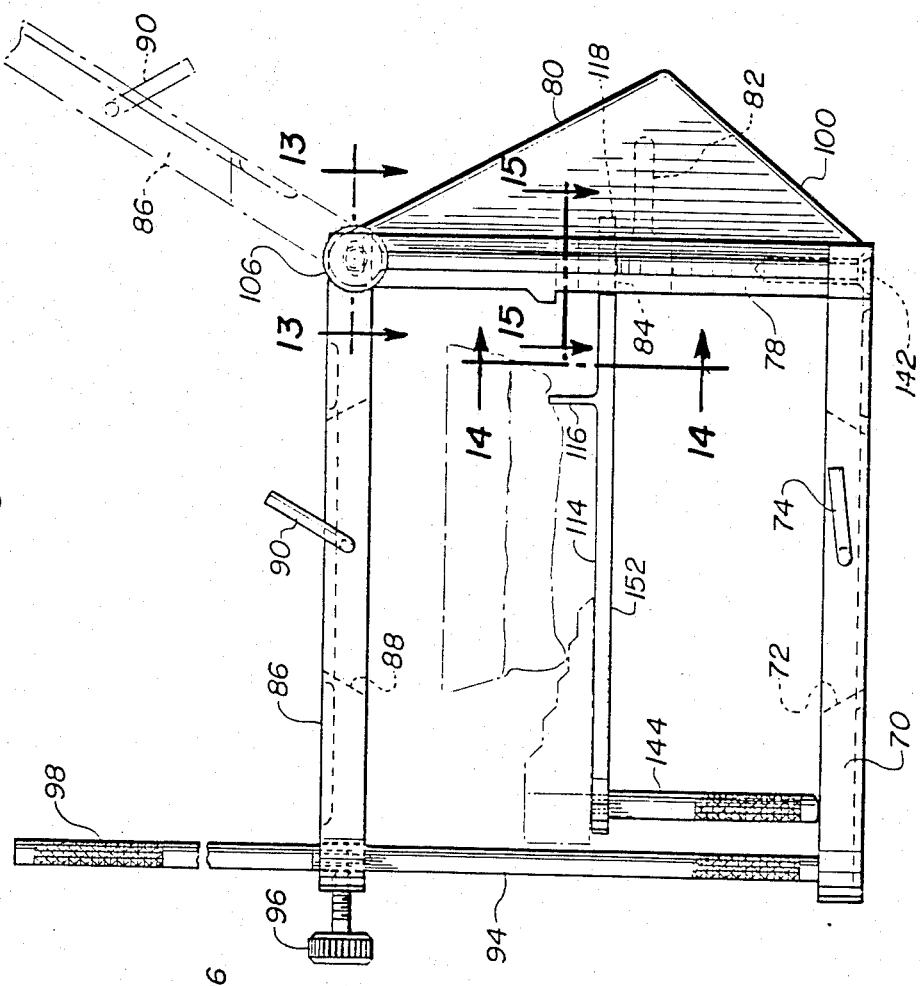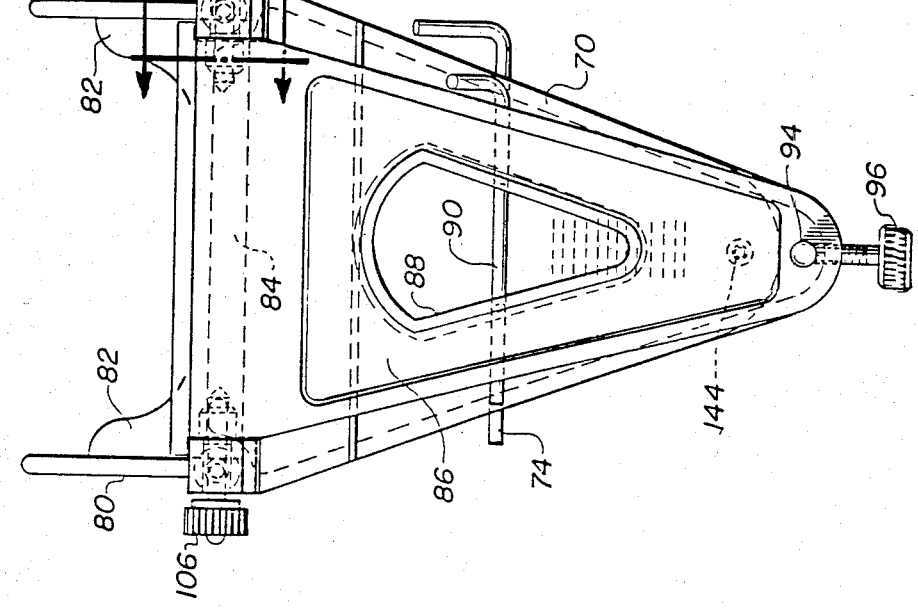

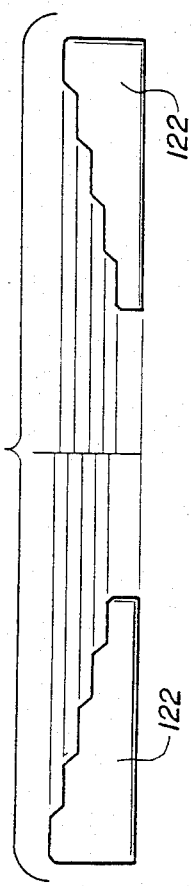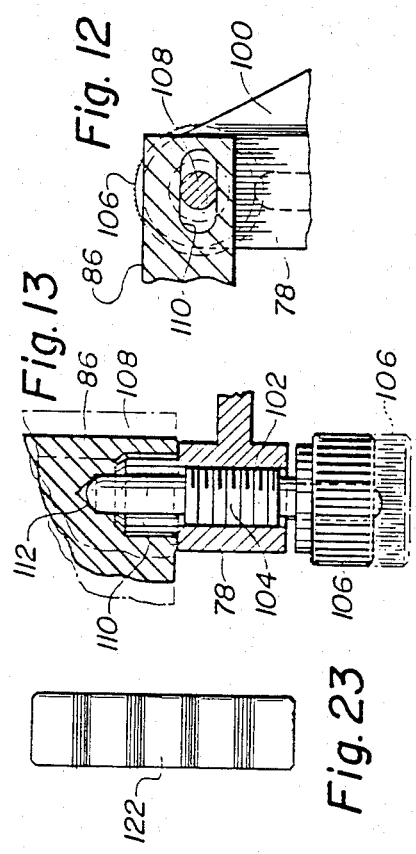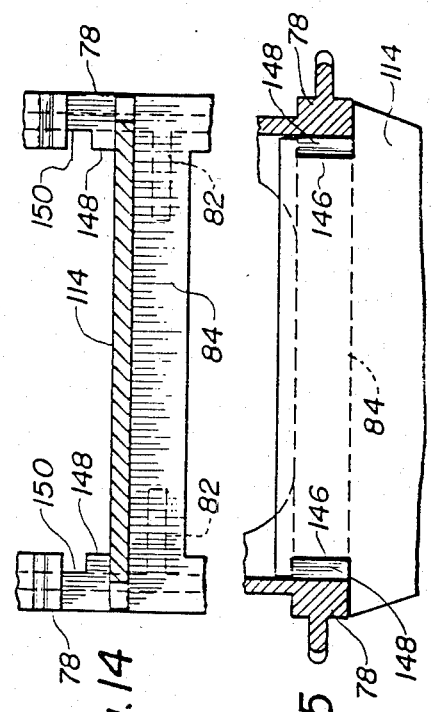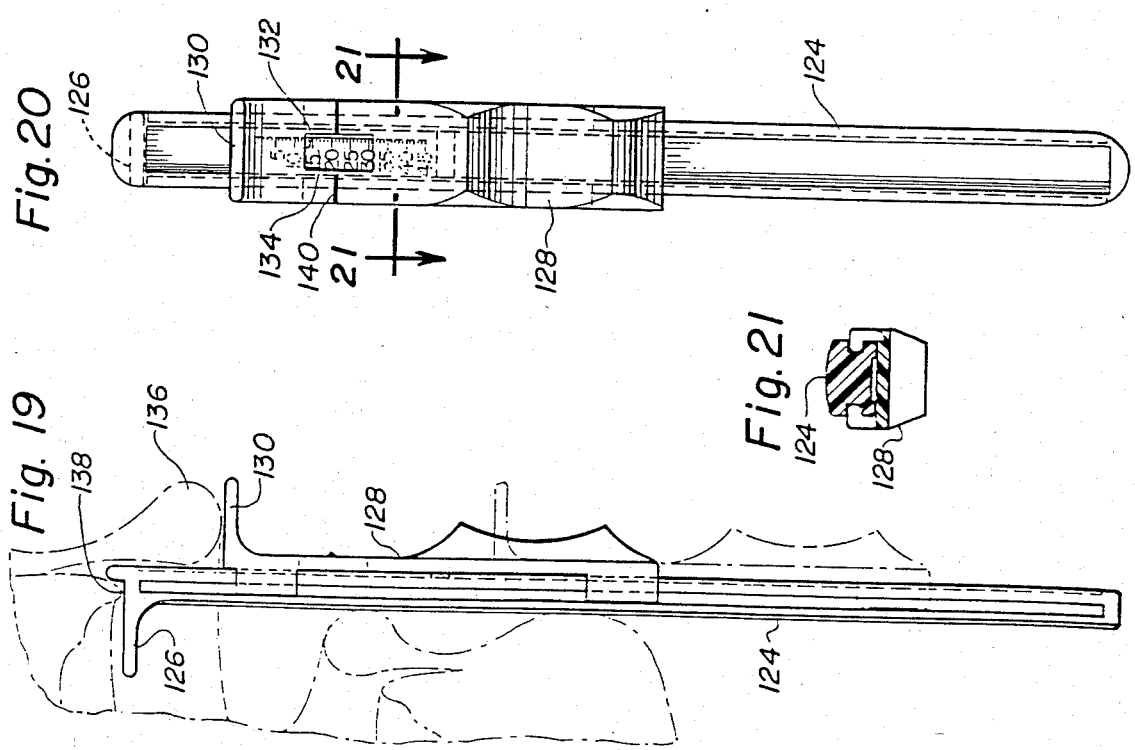

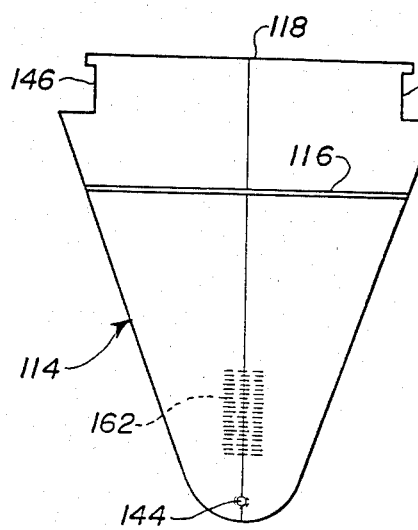
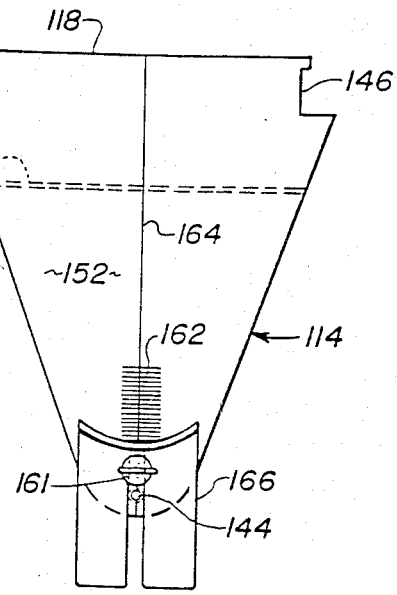
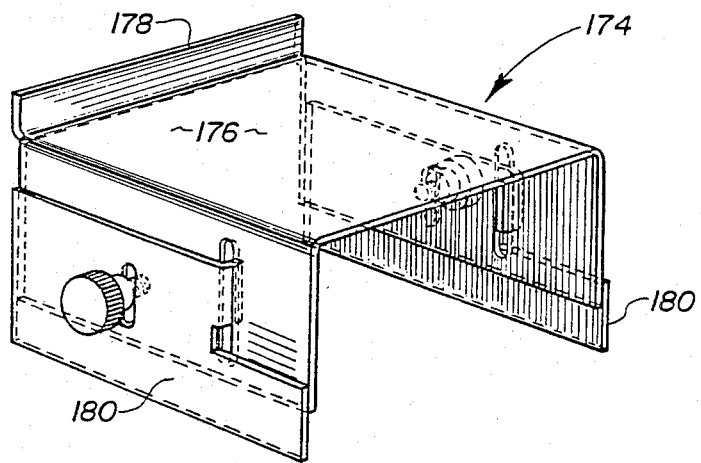
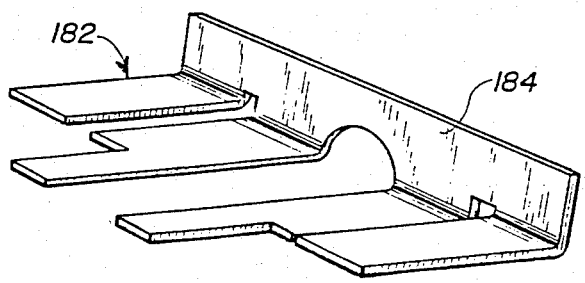
Fig. 16  Fig. 17  Fig. 18
Fig. 24
Fig. 25

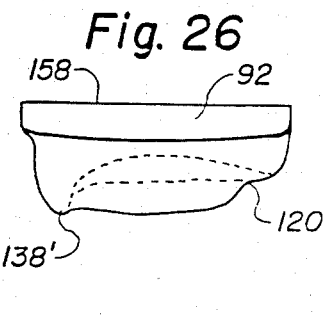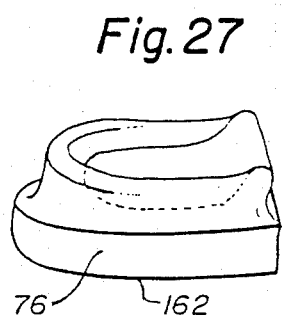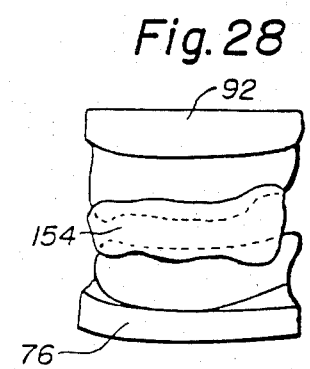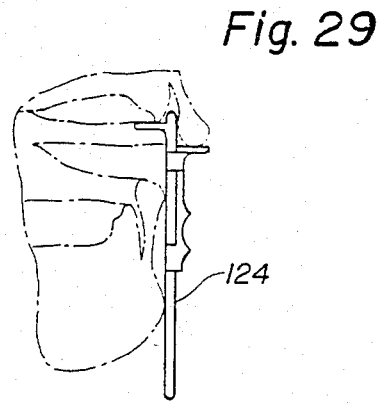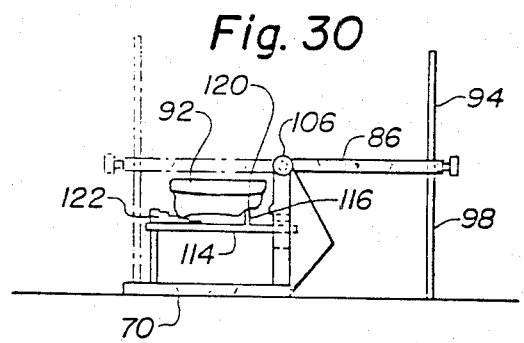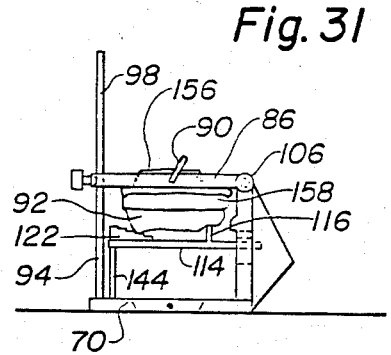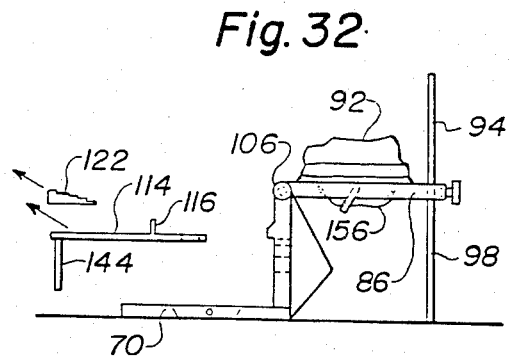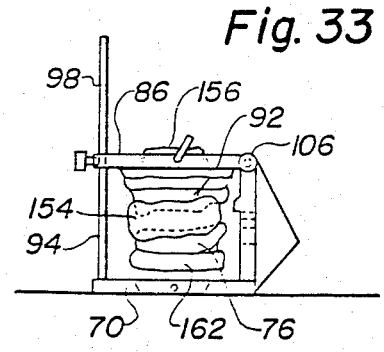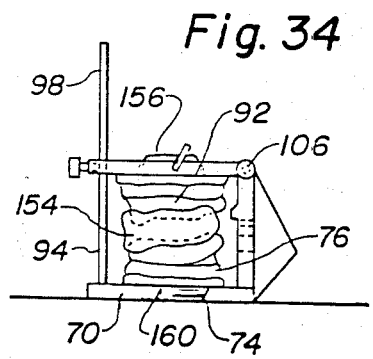

METHOD AND APPARATUS TO PRODUCE ARTIFICIAL TEETH FOR DENTURES

BACKGROUND OF THE INVENTION

The production of artificial dentures is an art which has existed for at least several hundred years and over that period has constantly been improved to achieve the ultimate goal of maximum comfort to persons wearing such dentures and close simulation to natural dentitions. One of the principal difficulties involved in the preparation of artificial dentures comprises the arranging of artificial teeth and connecting the same to denture base material to produce finished dentures. The majority of dentures made at the present time include the connection of individual artificial teeth to the denture base material and this is accomplished, in the main, by dental laboratories, but is by no means restricted to the same in that some dentists prefer to fabricate the dentures for their patients.

In general, the preparation of full dentures commences with taking impressions of both upper and lower edentulous arches, and establishing their relative position to one another both at rest and in function. These methods are described in texts and other publications, and result generally in the preparation of a "bite record" used by the dental laboratory from which a try-in is fashioned.

The impressions are taken by procedures well known to the art using alginate impression material or the like, and models of the patient's jaws and gums, known as casts are formed from setable materials such as certain gypsum material, commonly referred to as "dental stone". A baseplate next is formed upon the cast using a thermoplastic material in sheet form, by softening and adapting it over the cast. Upper and lower baseplates prepared in this manner are then used by the dentist to establish a bite record. The baseplates are introduced into the mouth of the patient, separated by soft wax which is deformed by the action of the patient's jaws as they are guided into their proper position by the dentist. The soft wax is modeled in a relatively rough labial contour of the teeth as they will be positioned in the finished denture, and the relationship between the jaws is transferred to a dental articulator which serves to hold the casts in the same relative position, as described in greater detail hereinafter. Also, certain measurements made with appropriate instruments determine the preferred vertical relation especially between the central, forward portions of a patient's gums on the respective jaws, known professionally as the "incisive papilla".

Individual posterior and anterior artificial teeth then are imbedded in wax material, known as "set-up wax," applied to the baseplates to conform to the surfaces determined by the "bite record." Then additional wax is applied between the gingival surfaces of the artificial teeth and the baseplates in a manner to resemble natural gum contours. The foregoing operations are performed while the casts are mounted in the upper and lower bows or members of an articulator which permits relative movement between the upper and lower sets of artificial teeth formed on the casts by the foregoing procedures and thereby enables a dental technician or dentist to provide desirable occlusion and function between the artificial teeth on the respective casts. Mounting such teeth on the cast or model by the foregoing procedure requires extensive skill and is relatively time-consuming. The elimination of such substantial consumption of time is an essential objective of the present invention.

After the above procedures have been completed, the baseplates and the contoured wax material and artificial teeth mounted thereon then are removed from the articulator respectively and may be tried in the mouth of the patient, if desired. With the upper and lower casts attached thereto, they are then invested in suitable molding compounds, generally of a gypsum nature. The baseplate and set-up wax are removed from the hardened investment by heating and softening methods to provide a cavity into which permanent denture base material is injected or molded for connection to the ridgelap and gingival surfaces of the artificial teeth by the well-known "lost wax" process.

The foregoing procedure is generally exemplary of the methods used at present to fabricate artificial dentures. Various modified steps of the procedure occur at present, but in general, it will be seen that one of the principal difficulties arising from the procedure comprises the mounting of individual artificial teeth upon the wax substrate to which they are attached and also to provide proper occlusion between the opposed masticating surfaces of the teeth in the upper and lower dentures.

One of the improvements offered by the present invention in at least one principal aspect comprises the use of full arch upper and lower sets of artificial teeth which are integrally connected together in said sets and opposite sides of each arch formation are braced to stabilize the shape. The teeth provided in said full arch sets have certain characteristics which attempt to resemble natural teeth, while at the same time, facilitating the molding of such teeth in molds which preferably are relatively simple. In this regard, it is to be noted that the use of full arch sets of artificial teeth to form dentures is not new from a basic standpoint. Previous attempts to simplify the formation of artificial dentures have included the use of such full arch sets of artificial teeth and typical examples of the same are found in such prior U.S. Patents as U.S. Pat. No. 1,814,717 to Maizner, dated July 14, 1931; U.S. Pat. No. 2,539,882 to Zilinski, dated Jan. 30, 1951; U.S. Pat. No. 2,768,440 to Elliott, dated Oct. 30, 1956; and U.S. Pat. No. 4,099,329 to Hawthorne, dated July 11, 1978.

In addition to the use of full arch sets of artificial teeth in the making of dentures as noted above, various procedures for the forming of dentures with the aid of articulators in order to attempt to minimize the amount of time consumed have been the subject matter of other prior U.S. Patents, including U.S. Pat. No. 1,814,717 to Maizner, dated July 14, 1931; U.S. Pat. No. 2,171,759 to Meyer, dated Sept. 5, 1939; and U.S. Pat. No. 4,189,837 to Stele, dated Feb. 26, 1980, as well as prior British Pat. No. 295,768 to Perks, dated Aug. 23, 1928 and prior German Pat. No. 508,921 to Kantorowicz, dated Oct. 2, 1930.

Further to facilitate the formation of artificial teeth with an enamel simulating layer, prior U.S. Pat. No. 1,547,643 to Clapp, dated July 28, 1925, illustrates a form of mold and technique to accomplish this, while prior U.S. Pat. No. 1,907,923 to Willis, dated May 9, 1933, is one example of a measuring device used incidental to determining desirable bite level between artificial dentures and thereby facilitate the comfort of using the same.

3

The characteristics and advantages of the present invention over the techniques and apparatus presently in use, as enumerated above, are set forth below in detail.

SUMMARY OF THE INVENTION

It is among the objects of the present invention to improve and simplify the technique of forming artificial dentures primarily by using full arch sets of artificial teeth and employing a process by which said teeth ultimately are fabricated as finished dentures by the employment of procedural steps and apparatus submitted to be improvements over the procedures and apparatus presently in use, both as enumerated above and as practiced presently by dentists and dental technicians in dental laboratories.

The full arch unitary sets of artificial teeth comprising an important and advantageous feature of the present invention, are the subject of the present application, the teeth in the anterior portion of the sets in particular being provided with interproximal spaces adjacent the gingival portions of the teeth for purposes of permitting denture base material to be positioned between the gingival areas and thus, resemble natural gums, and in regard to both the anterior and posterior teeth, the labial and buccal surfaces thereof have been formed to resemble the corresponding surfaces of natural teeth insofar as possible, but said surfaces have been shaped in a manner to readily permit the removal of the molded full arch sets of teeth from rigid molds without interference and with minimum requirements for finishing.

Ancillary to the foregoing object relative to the full arch sets of artificial teeth, the same are provided with stabilizing strut means extending between and connected to opposite sides of the U-shaped configuration of said full arch sets, the strut means comprising fingers extending radially from a central member and the ends of the fingers which are connected to certain of the posterior teeth are of minimal cross-sectional area to facilitate separating the same from the full arch sets of teeth prior to the final contouring of the lingual surfaces of the posterior teeth, as forth in detail hereinafter.

In performing the preferred process for forming dentures which include the full arch sets of teeth of the present invention, a number of apparatus units have been developed, together with the steps of the preferred procedures, all of which are the subject matter of another related application. However, to appreciate the significant novelty and advantages afforded by the use of the full arch artificial teeth of the present invention and for convenience, a relatively full description of the apparatus and process is included hereinafter in the present application.

Details of the foregoing objects and of the invention, as well as other objects thereof, are set forth in the following specification and illustrated in the accompanying drawings comprising a part thereof.

BRIEF DESCRIPTION OF THE DRAWINGS

FIG. 10 is a top plan view of an articulator of a simplified type for use in the process preferred for incorporating sets of teeth of the present invention in finished dentures.

FIG. 11 is a side elevation of the articulator shown in FIG. 10, as viewed from the right-hand side thereof, shown in said figure, FIG. 11 also including fragmentarily in phantom, an elevated position of the upper bow of the articulator.

FIG. 12 is a fragmentary vertically sectioned detail of the pivotal support for the upper bow, as seen on the line 12—12 of FIG. 10.

FIG. 13 is another horizontal sectional view, showing a detail of said pivotal means for the upper bow, as seen on the line 13—13 of FIG. 11.

FIG. 14 is a fragmentary vertical sectional view showing details for the support means of the mounting table, shown on the line 14—14 of FIG. 11.

FIG. 15 is a fragmentary horizontal sectional view of the support means shown in 14, but as seen on the line 15—15 of FIG. 11.

FIGS. 16, 17, and 18 respectively show top, side, and bottom views of the support table shown in FIG. 11.

FIG. 19 is a side elevation of a measuring instrument useful in conjunction with the present invention, as shown in the fragmentary portion of a human mouth, illustrated in phantom.

FIG. 20 is a front elevation of the instrument shown in FIG. 19.

FIG. 21 is a transverse sectional view of the instrument shown in FIG. 20, as seen on the line 21—21 thereof.

FIG. 22 is a composite side elevational view of a pair of stepped wedge-like support members used in conjunction with levelling an upper cast with respect to the support table and being disposed between said table and the forward portion of the upper cast selectively in increments of one millimeter.

FIG. 23 is a top plan view of one of the wedge-like members shown in FIG. 22.

FIG. 24 and 25 respectively are respective views of different types of alternate support means used in articulators not illustrated in the foregoing views, in lieu of the supporting table actually shown in said views.

FIG. 26 is a side elevation of an exemplary upper gum or jaw of a patient and comprises a dental cast thereof.

FIG. 27 is a perspective view of an exemplary lower cast simulating the lower jaw of a patient.

FIG. 28 is a side view of the upper and lower casts of FIGS. 26 and 27, being joined in operative relationship by means of a jaw-relation bite record, the elements shown respectively in FIGS. 26-28 normally being supplied by a dentist for purposes of utilizing the present invention.

FIG. 29 is a view similar to FIG. 19 and showing the instrument of FIGS. 19 and 20 respectively engaging the lower end of the upper lip and the forward portion of the upper jaw or gum of a patient to provide a required measurement incident to the use of the wedge member shown in FIGS. 22 and 23.

FIGS. 30-41 successively illustrate various steps of a preferred method for incorporating the full arch sets of upper and lower artificial teeth of the invention into finished dentures, said steps being described in detail hereinafter in the specification.

DETAILED DESCRIPTION OF THE PREFERRED EMBODIMENT

The present invention includes a number of related facets all leading to the common goal of producing satisfactory, reasonably life-like artificial dentures which include full arch unitary upper and lower sets of artificial teeth, thereby resulting primarily in a substantial saving in time to produce the so-called dental "set-ups" which, as such, are then processed by conventional methods or otherwise into finished dentures. In the foregoing, reference has been made to the great skill and amount of time required to place individual artificial teeth on baseplates with wax which is sculptured to provide aesthetic configurations resembling natural gums, and it is in this area of the production of artificial dentures that the present invention provides very substantial advantages.

As is evident from the prior art referred to hereinabove, the use of full arch sets of artificial teeth is not new per se. Attempts have been made by others to commercialize full arch sets of molded artificial teeth, but for the most part, these have been unsuccessful. Possibly a major reason such prior commercial attempts have not been successful has been due to an inability to produce such teeth economically, while retaining acceptable aesthetics with practical adaptability to dental laboratory utilization. The present invention has overcome this difficulty in what is submitted to be a practical and aesthetically acceptable product.

One of the advantageous features of the sets of teeth of the present invention comprises the repositioning of many of the teeth from the angles normally chosen for a tooth arrangement for artificial dentures so that the teeth can be mass-produced in rigid molds without formation of objectionable parting lines. This has involved reshaping the teeth to maintain a pleasing aesthetic appearance, as well as realigning them. The anterior teeth, including the central and lateral incisors, for example, have the facial or labial surfaces thereof slanting outward at the incisal edges so the same can be withdrawn from a rigid mold without leaving a parting line on such labial surfaces. The posterior teeth have their facial or buccal surfaces slanting inward toward the occlusal surfaces so they may be withdrawn from another area of the molds without leaving a parting line. The canines are treated in an unusual way by slanting their facial or labial surfaces outwardly at the incisal edges in line with the other anterior teeth, as will now be described in detail relative to the drawings.

FULL ARCH SETS OF ARTIFICIAL TEETH

Figure 1:
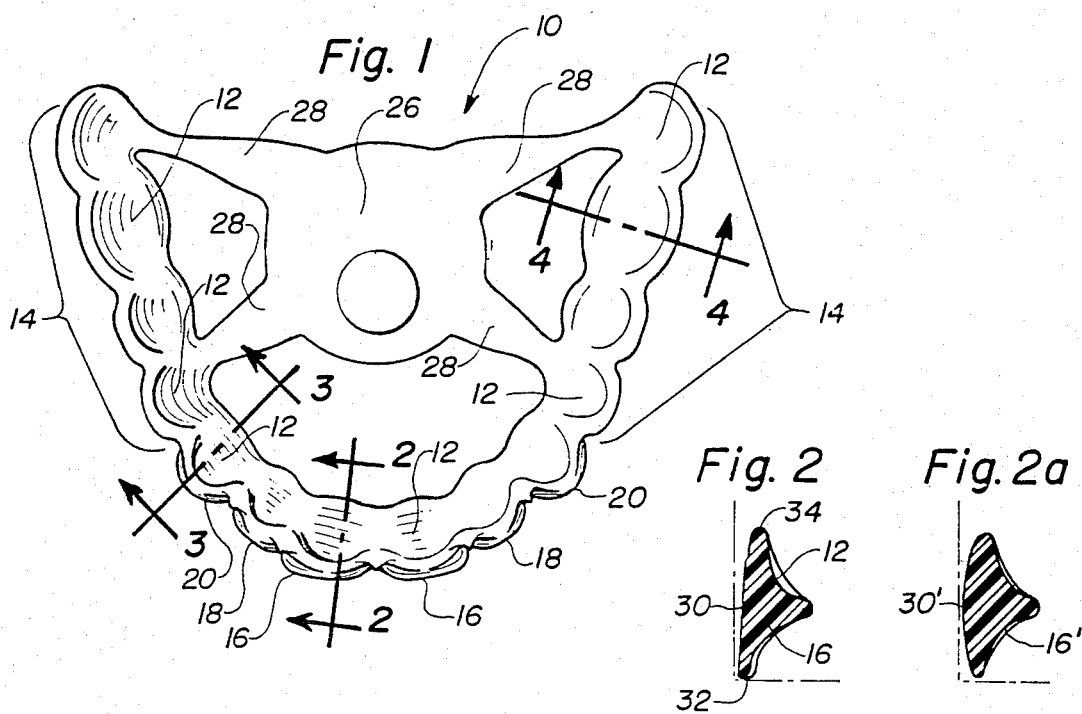
FIG. 1 is a top plan view of an exemplary full arch unitary set of upper artificial teeth, embodying the principles of the present invention.
Figure 9:
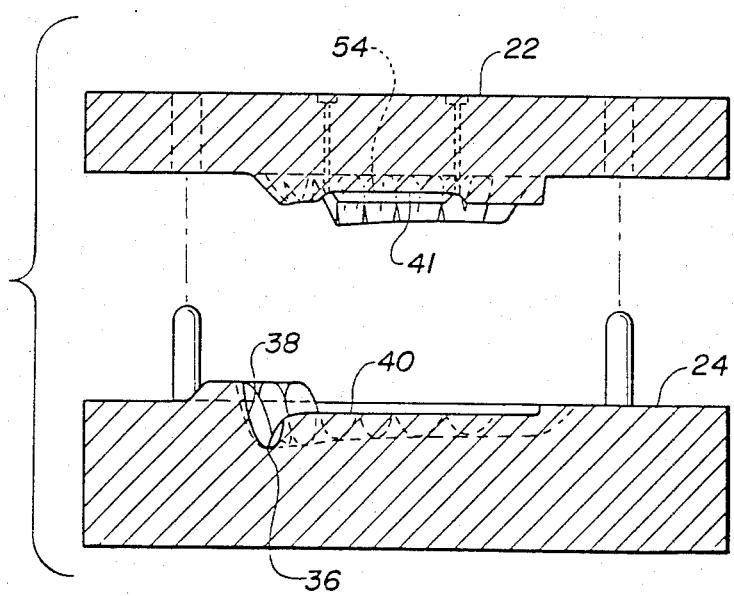
FIG. 9 is a vertical sectional view of an exemplary set of upper and lower dies in which full arch sets of upper and lower artificial teeth are capable of being molded to have the general characteristics especially shown in FIGS. 6-8.
Figure 35:
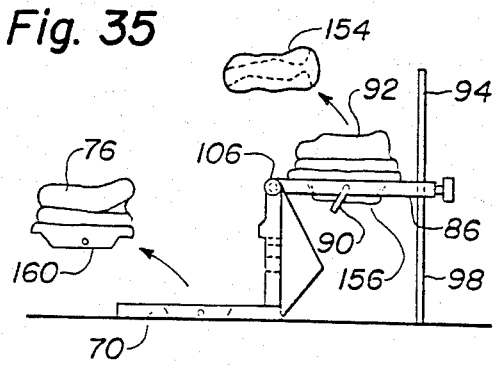

Referring to FIG. 1, an exemplary full arch set of artificial teeth is illustrated in top plan view and shows the ridgelap depressions 12 of the four posterior teeth 14 at opposite sides of the set 10, and include first and second molars and first and second bicuspids, together with the six anterior teeth at the intermediate portion of the arch configuration and comprising a pair of central teeth 16, a pair of lateral teeth 18, and a pair of canines 20, all arranged to be molded integrally in rigid molds, such as illustrated in exemplary manner in FIG. 9, and comprising a rigid upper mold 22 and a matching lower mold 24, details of which are described to a greater extent below.

To maintain the arched configuration of the exemplary set of upper teeth 10, stabilizing strut means are attached to the inner surfaces especially of the posterior teeth and comprise a central member 26 from which radial fingers 28 extend somewhat in octopus manner. It will be noted the fingers 28 taper outwardly from the central member 26, the smaller ends of the fingers being connected to the posterior teeth in a manner that may be readily severed therefrom after the stabilizing function of the strut means has ceased, such as when the full arch configuration of teeth has been attached to baseplates or other means described hereinafter in detail.

Figures 2, 2A:
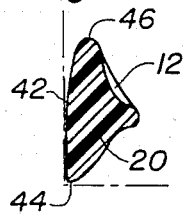
FIG. 2 is a sectional view taken on the line 2—2 of FIG. 1 and showing the cross-section of a central tooth of the set of full arch teeth, shown in FIG. 1, the labial face of the tooth sloping in at the gingival and out at the incisal, to facilitate removing the teeth from a rigid mold.
FIG. 2a is a view corresponding to FIG. 2, but showing the cross-sectional shape of a normal central artificial tooth in which the labial face of the tooth extends inwardly at the incisal, which would impair the removal of the tooth from the type of mold preferred to manufacture the teeth of the present invention.

To provide illustrations of the manner in which the present invention has effected repositioning of many of the teeth from angles normally chosen for a tooth arrangement for an artificial denture, attention is directed to FIG. 2, which is a cross-section taken on the line 2—2 of FIG. 1 and illustrates a vertical section of a central tooth 16, having a ridgelap depression 12 and the facial or labial surface 30 sloping or slanting outward at the incisal edge 32 from the gingival end 34 to facilitate withdrawing the molded teeth from a rigid mold, such as illustrated in exemplary manner in FIG. 9 with respect to the lower mold 24 wherein the molding recess 36 forms the gingival end 34 of the central teeth 16, for example, and in which the surface 38, comprising a series of adjacent molding cavities, forms the labial faces 30 of the central teeth. Preferably, the molding cavities 40 and 41 respectively in the lower and upper molds have parting lines at the incisal ends of the anterior teeth and occlusal surfaces of the posterior teeth.

From FIG. 2, it also will be seen that the labial surface 30 of central tooth 16 slopes backward from the incisal end, away from the vertical reference line shown in phantom, at an angle of about 0° to 10° for at least about 70 percent of the length thereof.

An exemplary illustration of a substantially conventional artificial central tooth 16' is shown in FIG. 2a and, as shown in FIG. 2, the labial surface 30' thereof is illustrated with reference to ordinate phantom lines at right angles to each other, the vertical line being the reference line with respect to the slanting or sloping of the labial surfaces of the teeth. In FIG. 2a, it will be seen that the labial surface 30' of a central tooth slopes inwardly at both the gingival and incisal ends and would present difficulties in utilizing a single pair of rigid molds in which the parting line is at the incisal ends of the teeth, whereby the exemplary tooth shown in FIG. 2a could not be withdrawn from molds of the type employed to form the exemplary central tooth 16 shown in FIG. 2.

Figures 3, 3A:
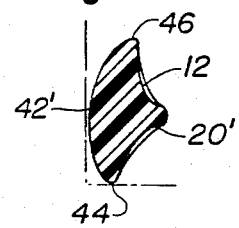
FIG. 3 is a vertical sectional view of a canine tooth of the set shown in FIG. 1, as seen on the line 3—3 thereof, and illustrating as in regard to FIG. 2, the manner in which the canine tooth slopes inwardly at the gingival and outwardly at the incisal to facilitate the removal of the same from the mold.
FIG. 3a is a view similar to FIG. 3, but shows a sectional view of a more or less conventional canine artificial tooth in which the labial surface extends inwardly at the incisal, as well as at the gingival.

With reference to FIGS. 3 and 3a, it will be seen that in FIG. 3, taken on the line 3—3 of FIG. 1, a canine or so-called "eye tooth" 20 is shown, in which the facial or labial surface 42 slopes outwardly at the incisal end 44 and inwardly at the gingival 46, thus facilitating the molding thereof by rigid molds, as described above with respect to the central tooth 16, shown in FIG. 2. In contrast, the conventional canine tooth 20', shown in FIG. 3a, has an outward or labial surface of curved configuration extending inwardly both at the incisal 44 and gingival 46 and would similarly present difficulties in the type of rigid molds employed in the invention as described above with respect to FIG. 2a. With respect to labial surface 42, it will be seen from FIG. 3 that the same slopes backward from the incisal end, away from the vertical reference line shown in phantom, at an angle of about 0° to 10° for at least 70 percent of the length thereof.

Figures 4, 4A:
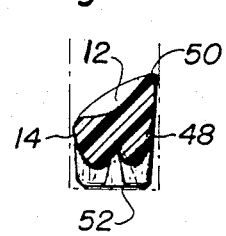
FIG. 4 is a sectional view of a posterior tooth formed in accordance with the invention, as seen on the line 4—4 of FIG. 1, and illustrating labial surfaces which slope inwardly from the gingival toward the occlusal.
FIG. 4a illustrates a similar cross-sectional shape of a conventional posterior artificial tooth in which the labial surface thereof is substantially perpendicular to the occlusal plane illustrated by the bottom horizontal phantom line.

Considering the posterior teeth 14 by referring to FIG. 4, which is taken on the line 4—4 of FIG. 1, it will be seen that the outer or buccal surface 48 slopes outwardly at the gingival 50 of posterior tooth 14 and inwardly at the occlusal end 52 to facilitate the removal from the molds 22 and 24, and especially the mold 22 and in which the mold section 54 forms the occlusal surface 52 of the posterior teeth 14. The above-described slope of the buccal surface 48 in FIG. 4 is illustrated with reference to an exemplary phantom ordinate line to illustrate the sloping arrangement. The ordinate line also is illustrative of a planar member which, when laid against the buccal surface, will show that the buccal surface slopes away from said member at an angle of about 0° to 10° for about 90 percent of the height of the posterior tooth. In contrast, referring to FIG. 4a in which a conventional similar posterior tooth 14' is shown, it will be seen that the conventional buccal surface 48' slopes inwardly somewhat at the gingival end 50 and substantially inward at the outer portion of the occlusal surface 52, which arrangement would present difficulties in utilizing molds of the type shown in FIG. 9.

Figure 5:
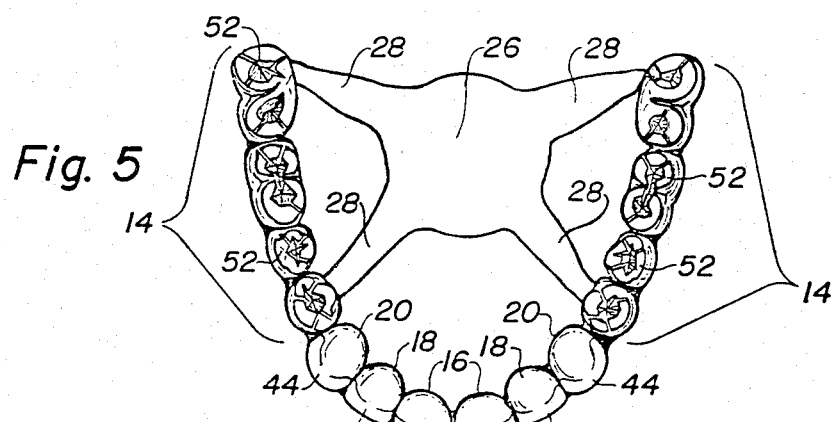
FIG. 5 is a plan view of the occlusal surface of the exemplary full arch set of artificial teeth shown in FIG. 1.
Figure 6:
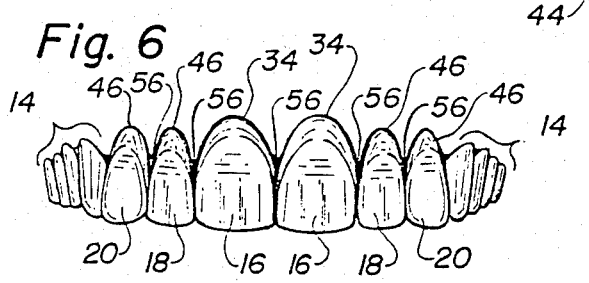
FIG. 6 is a front elevation of the full arch set of artificial upper teeth shown in FIG. 1.

FIG. 5 is an exemplary bottom plan view of a full arch set of upper artificial teeth to illustrate the occlusal and incisal ends of the posterior and anterior teeth, said view being the opposite of that shown in FIG. 1. Referring to Fig. 6, which is a front elevation of the exemplary full arch set of upper artificial teeth, shown in FIGS. 1 and 5, it will be seen in this view that the slope of the buccal surfaces of the posterior teeth 14 is well illustrated and it is to be understood that the shape, and especially the outer labial surfaces of the lateral teeth 18 is substantially similar to that of the canine or cuspid teeth 20. Another important feature of the full arch set of artificial teeth which adapts its use with the invention is also illustrated in FIG. 6 in which it will be seen that pronounced interproximal triangular spaces 56 are illustrated for purposes of effecting desirable aesthetic contours to cause these artificial teeth to closely resemble similar surfaces of natural teeth, at least portions of said interproximal spaces 56, as well as the gingival end portion of the anterior teeth being partially covered by portions of the denture base material in the finished dentures in a manner to resemble natural gums and teeth.

Figure 7:
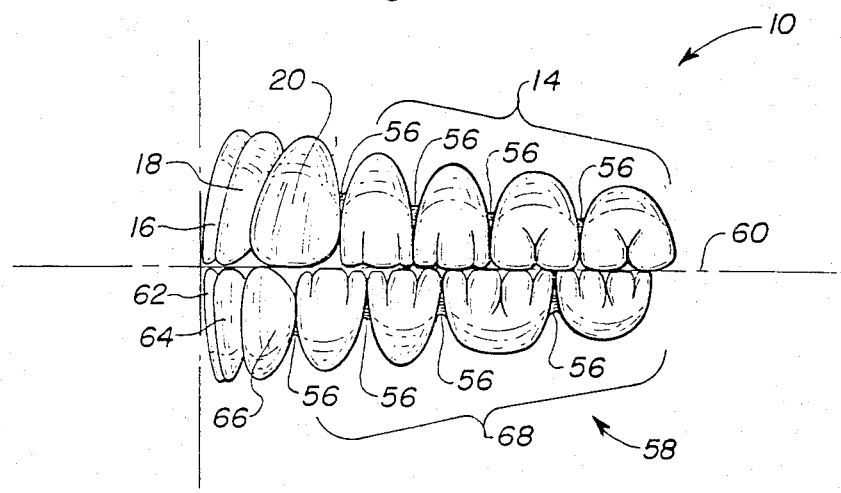
FIG. 7 is a side elevation of an exemplary full arch set of upper and lower artificial teeth, including employed in details the present invention and shown in occlusion with respect to each other, said view showing in particular the sloping labial surfaces of the central teeth of the respective sets thereof, which correspond generally to FIG. 2.

Referring to FIG. 7, it will be seen that there is illustrated therein a full arch set of upper artificial teeth 10 and a full arch set of lower artificial teeth 58, both shown in side elevation and disposed in operative relationship with respect to each other along an occlusal plane 60, shown in phantom. Preferably, the incisal edges of the anterior teeth which are shown at the left-hand end of FIG. 7, and the occlusal surfaces of the posterior teeth shown in the right-hand portion of FIG. 7, commonly abut the occlusal plane 60 and, while the teeth of both types are shaped to closely resemble the outer labial surfaces of the anterior teeth and the outer buccal surfaces of the posterior teeth, the occlusal surfaces of the posterior teeth, in particular, preferably are of the so-called flat plane type in that the occlusal surfaces do not interdigitate.

Figure 8:
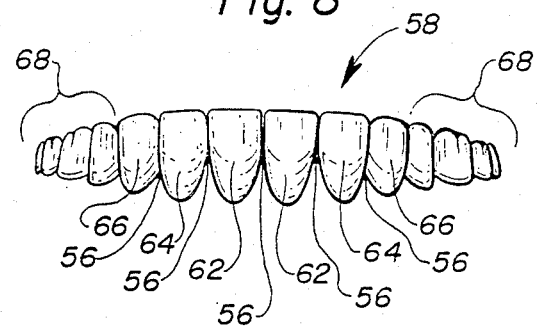
FIG. 8 is a front elevation of an exemplary full arch set of lower artificial teeth and illustrating as in FIG. 6 the indented interproximal surfaces adjacent the gingival ends of the teeth.

Referring to FIG. 8, in which a front elevation of the full set of artificial lower teeth 58 is illustrated, it will be seen that the corresponding central teeth 62, lateral teeth 64, and canine or cuspid teeth 66 are respectively somewhat narrower than the corresponding teeth of the upper set 10, as shown, for example, in FIG. 6, thereby harmonizing with this characteristic of natural teeth. The groups of four posterior teeth 68, however, as seen from FIG. 7, are not narrower than the corresponding teeth of the upper set 10. In particular, however, it will be seen that interproximal spaces 56 are provided in the lower set of teeth 58 for the same purposes as described above with respect to the corresponding interproximal surfaces of the upper set of teeth 10.

For purposes of simplifying the molding of full arch sets of artificial teeth, it is preferred, in accordance with the invention, that a relatively simple set of cooperating upper and lower molds 22 and 24 be employed. However, it is readily possible to use so-called 3-part molds, embodying principles of the type shown in the prior U.S. Pat. No. 1,547,643 to Clapp, dated July 28, 1925, and in which there is shown a so-called shader mold which is used for purposes of including on the labial or front surfaces of the anterior teeth, a thin layer of more transparent plastic material than that with which the main body of each tooth is formed for purposes of simulating more closely natural teeth which have an outer layer of more transparent enamel over an opaque body of the tooth, and to this end, the exemplary molds shown in FIG. 9 may be supplemented by a suitable third, shader mold.

For a complete understanding of the preferred procedure for using the sets of full arch teeth incident to preparing finished dentures, special apparatus and procedures which have been developed and comprise the subject matter of a separate related application, are included in this application as follows:

For purposes of fabricating the above-described full arch sets of artificial teeth into finished dentures, a special and very simplified type of articulator has been developed, details of which are shown in FIGS. 10–13. Referring especially to FIGS. 10 and 11, the articulator comprises a lower bow or base member 70, which may be disposed upon any suitable supporting surface, such as a counter or bench. It is generally triangular in shape, as seen in FIG. 10, and has a central, somewhat triangular opening 72 formed therein and a securing pin 74 removably extends through aligned openings in the portions of the base 70, which are on either side of the central opening 72, this apparatus being used in conjunction with securing the lower cast or model 76 of a patient's mouth to the base, one exemplary illustration of the same being shown in FIGS. 27 and 28.

Extending upwardly from the rear portion of the base 70, at opposite sides thereof, is a pair of support members 78, such as shown in FIGS. 11–15. Said support members have rearwardly extending wing-like extensions 80 and bracing fillets 82, shown in FIGS. 10 and 11, connected to a transverse support bar 84, which is integrally connected at its ends to support members 78, as best shown in FIG. 14. The purpose of the bar 84 is set forth below.

Hingedly connected to the upper ends of support members 78 is an upper bow or member 86 which also has a somewhat triangularly shaped opening 88, formed somewhat centrally thereof and another securing pin 90 extends transversely through aligned openings extending transversely through opposite side portions of the upper bow at either side of the opening 88. The arrangement just described is for purposes of securing to the upper bow 86 an upper cast or model 92 of a patient, one particular example of which is shown in FIGS. 26 and 28. In FIG. 11, the upper bow 86 is shown in full lines in its normal operative position, while in phantom, the same is shown in elevated position. A post 94 is mounted for vertical adjustment within an opening in the forward portion of upper bow or member 86 as clearly shown in FIGS. 10 and 11, adjustment being secured by a thumb screw 96, and is operable to maintain the upper bow 86 in normal substantially horizontal position which is parallel to the base 70. An upper extension 98 is connected axially to the post 94 and is for purposes of holding the upper bow in full-extended, pivotal position, such as shown, for example, in FIGS. 30–36. Similarly, the triangular shape of the extensions 80 on the support members 78 has a lower rearward edge surface 100, by which the articulator may be supported when the surfaces 100 are disposed on a supporting surface, for any desired purpose.

Although the articulator shown in FIGS. 10–13 is of a very simple nature, especially as compared to other more sophisticated articulators which in particular frequently have elaborate adjustable pivot means, the pivot means of the instant articulator permit at least a limited amount of anterior, posterior, and opposite lateral movements of the upper bow or member with respect to the centric position to permit a desirable amount of milling movements between sets of full arch artificial teeth when respectively supported by the upper bow 86 and base 70, as described in detail hereinafter, as well as pivotal movement of the bows about a horizontal axis. Such limited milling movement is permitted by details shown particularly in FIGS. 12 and 13, and in which the upper ends of the support members 78 are each provided with a threaded opening 102 to receive intermediate threaded portions of threaded thumb screws 104, having knurled knobs 106 on the outer ends thereof and the opposite ends of said screws having a smooth, cylindrical pivot extension 108 of less diameter than the threaded portion 104. Opposite sides of the rear end portion of the upper bow 86 have short elongated recesses 110 of limited length and depth within which the pivot extensions 108 are disposed.

The inner ends of the recesses 110 have a central socket 112, also of limited depth, extending axially inwardly a limited amount for purposes of receiving the terminal end of the pivot extensions 108 when the thumb screws 104 are threaded to the full permitted extent inwardly, whereby a solely pivotal movement about a transverse axis is afforded the upper bow without milling movement. However, by backing off the thumb screws 104 sufficiently until the ends of the extensions 108 are disposed only in the short recesses 110, said limited amount of milling movement of the upper bow with respect to the base or lower bow may be effected, as can be visualized from the length of the recess 110, shown in FIGS. 12 and 13. This amount of movement is adequate to effect a highly useful and practical milling movement.

An important element of the articulator comprises a mounting table 114 which is planar and preferably triangular in shape as shown in FIGS. 16 and 18. One surface of the mounting table 114 is provided with a mounting bar or rib 116, which is parallel to the rear edge 118 of mounting table 114 and is disposed a limited distance therefrom for purposes of having the hamular notches 120 of the upper cast 92, see FIG. 26, positioned thereon to facilitate the alignment and height of said cast with the mounting table 114.

This situation requires the use of a measurement to facilitate the full positioning of the upper cast or model on said table and wedge blocks 122, see FIG. 22, effect such positioning. Said blocks have stepped faces arranged predetermined distances apart in elevation, in even or odd increments of two millimeters apart, and in view of there being a pair of such wedges respectively with the stepped surfaces, one has surfaces offset one millimeter with respect to steps on the other, and thereby selectively provide, for example, one millimeter adjustments in the stepped surfaces while using one or the other of the wedge blocks 122, such use being illustrated and described hereinafter relative to additional figures.

The aforementioned measurement referred to immediately above can be effected by an instrument such as that illustrated in FIGS. 19–21 and comprising an elongated bar 124 at the upper end of which a lateral blade 126 is formed, the bar accommodating a slide 128, which, at its upper end, has another blade 130 extending laterally therefrom and a viewing opening 132 also being formed in said slide for purposes of observation of scale indicia 134 formed on one face of the bar 124, as clearly shown in the upper portion of FIG. 20. Referring to FIG. 19, there is fragmentarily illustrated therein, in phantom, a sectional outline of an upper lip 136 of a patient and the central forward portion 138 of the gum of the upper jaw of a patient, which is known as the incisive papilla.

The distance between the lower edge of the upper lip and the incisive papilla is measured on the scale 134 and is indicated by the reference line 140 on the slide 128, and the reading opposite the reference line indicates the distance the incisive papilla on the forward portion 138' of the upper cast, shown in FIG. 26, must be spaced from the upper surface of the support table 114, as viewed in FIG. 11, and from which the support bar 116 extends perpendicularly. Such spacing is accomplished by utilizing a selected stepped surface of one of the wedge blocks 122 which corresponds to said measurement and results in a positioning of the upper cast on the support table, as shown in FIG. 30.

Hamular notches in the upper casts or models of a patient's upper jaw have been used heretofore incident to leveling the cast relative to a bench top in a dental laboratory. As far as is known, however, such notches have not been used heretofore in conjunction with a positioning or support table. Also, while the aforementioned measurement between the incisive papilla of an upper cast or model and the lower edge of the upper lip of a patient has been used heretofore to establish a plane in the anterior region of a cast, such measurement has not been used as far as known to position said incisive papilla of the cast relative to a support table, especially in conjunction with the stated use of the hamular notches of the cast. Such an overall combination is believed to be novel and highly effective to produce satisfactory artificial dentures by the further procedures described herein.

The mounting table 114 is detachably and reversibly positionable upon the lower bow or base 70 of the articulator and the support members 78 which are affixed to the rear edge of the base 70 at opposite sides thereof by any suitable means, such as screws 142. When the table is to be mounted as shown in FIG. 11, with the mounting bar 116 extending uppermost, a reversible supporting pin 144 is threadably connected to the forward end of the table by being threaded into a suitable hole to support the forward end upon base 70. The rearward portion of table 114 rests upon transverse support bar 84, as shown fragmentarily in FIG. 14, and thereby supports the mounting bar 116 uppermost for disposition of the upper cast 92 thereon in the manner shown in FIG. 30. In order to prevent sidewise movement of the table with respect to the base 70, opposite sides of the rearward portion of the table 114 are provided with notches 146, which receive lugs 148 formed on the inner surfaces of the support members 78. Said members also are provided with notches 150, see FIG. 14, through which the rear edge of the table 114 may pass incident to disposing the notches 146 with respect to the lugs 148.

The table 114 is reversible in order that the planar surface 152 thereon may be disposed uppermost, when, for example, the upper full arch set of artificial teeth 10 is to be mounted operatively with respect to the upper cast or model 92 by procedures described hereinafter. To accomplish this, table 114 is removed from the position shown in FIG. 11 and is reversed to dispose the mounting bar 116 in a depending position, such as shown, for example, in FIGS. 36-38, the supporting pin 144 being unthreaded from the position shown on the table in FIG. 11, and is threaded into the opposite surface of the table and thus, disposes the table 114 in opposite parallel position with respect to the base 70 from that shown in FIG. 11.

DENTURE FORMING METHOD AND PROCESS

In the introductory portion of this specification, reference has been made to the formation of upper and lower casts or models 92 and 76 which, conventionally, are formed by a dentist and used by the dentist or sent to a laboratory for formation of the dentures by the employment of such casts or models. In addition, the dentist conventionally provides a jaw relation bite record 154, which consists of a plastic material of certain wax compositions or the like and, after being softened, is capable of being inserted into a patient's mouth between the upper and lower jaws and especially the gum portions thereof to impress said gums into the material and, after cooling to stabilize the bite record, forms at least a temporary relationship record to establish the relative vertical positions of the natural jaws with respect to each other and upon which artificial dentures are to be mounted so as to fit comfortably and be operable to masticate food while being retained solely by suction or gravity upon the patient's gums.

It is obvious that natural teeth in human dentitions space the gums vertically apart a predetermined distance, and it is preferable that this distance or one very close to it in measurement be used to space apart the upper and lower casts or models shown in FIG. 28 by means of the jaw relation bite record 154. Having been furnished either the upper and lower casts or impressions by which the casts may be formed, as well as the jaw relation bite record, a dentist or technician is then in position to proceed in accordance with the principles of this invention to fabricate a set of upper and lower dentures which include respectively full arch upper and lower sets of artificial teeth 10 and 58, such as shown in FIG. 1-8, by means of the following steps, illustrated sequentially in FIGS. 29-41:

Having obtained the required vertical spacing between the incisive papilla 138 and the lower edge of the upper lip 136, the upper cast or model 92 is mounted in the articulator, as shown in FIG. 30, in which the upper bow or member 86 has been pivotally moved 180° to the inoperative position shown in FIG. 30, and thereby enable the upper cast or model 92 to be mounted upon the table 114, with the hamular notches 120 positioned upon the support bar 116, and a selected stepped surface of the wedge block 122 has been placed upon the table 114 to support the incisive papilla the required distance from the upper surface of the table, as determined by the measuring instrument of FIGS. 19-21, so as to establish the upper cast in a position to receive the full arch set of upper artificial teeth by the procedures subsequently described.

The next step is shown in FIG. 31, in which the upper bow has been pivoted to operative position with respect to the table 114 by the upper bow being accurately positioned above base 70 by means of the post 94, whereupon settable attaching material 156, such as plaster, dental stone, or other gypsum-like material is disposed within the opening 88 of the upper bow so as to surround the pin 90 and be attached to the surface 158 of upper cast 92. The material 156 will operatively cure in a short period of time, such as twenty minutes, more or less, following which the steps shown in Fig. 32 take place, which comprises removing the table 114 and wedge block 122, as well as pivoting the upper bow 86 to inoperative position.

The foregoing step is followed by attaching the jaw relation bite record 154 to the upper cast or model 92 and also attaching the lower cast 76 to the bite record 154, as shown in FIG. 33. In this position, the lower cast 76 is in position to be attached to the base 70 of the articulator by additional settable material 160 of the same type as material 156, and illustrated in FIG. 34. Usually, when applying the material 160 to the base 70 and lower cast 76, the assembly shown in FIG. 33 is manually reversed while holding the upper bow 86 on base 70 in the relationship shown in FIG. 33 so that the material 160 may be poured through the opening 72, see FIG. 11, of base 70 and into engagement with the surface 162 of the lower cast and then permitting the material to set within the opening 72 and around the securing pin 74, which brings us to the step shown in FIG. 35, in which the upper bow 86 is pivoted to inoperative position with the upper cast 92 is secured thereto. The bite record 154 is removed from both casts and the lower cast 76 with its attaching means 160 is removed from the base 70.

Figure 36:
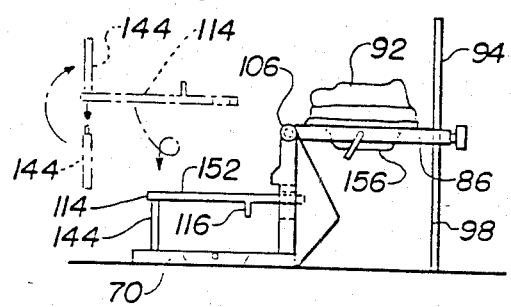
Figure 37:
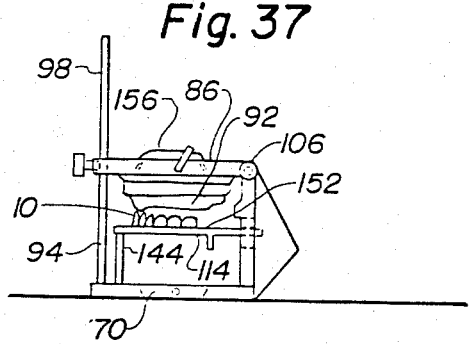

The next step comprises replacing the mounting table 114 in reversed position to that shown in FIG. 11, for example, as well as FIGS. 30 and 31, in order to dispose the planar surface 152 of said table uppermost, as shown in FIG. 36, it being understood that the supporting pin 144 also is reversed so as to engage base 70 and thereby support the planar surface 152 in proper position as shown in FIG. 37 to receive a full arch set of upper artificial teeth 10 with the incisal and occlusal surfaces of the anterior and posterior teeth precisely upon the upper surface 152 and in desired position with respect to the upper cast or model 92, as indicated by the spaced indicating lines 162 and median line 164 inscribed upon the surface 152 of the table 114, as shown in full lines in Fig. 18.

The foregoing positioning of the upper set of teeth 10 is accomplished by use of the upper cast or model 92 when supported by the upper bow or member 86 as shown in FIG. 37, but before the teeth 10 are placed as shown. Chiefly by sighting, an imaginary perpendicular line is dropped from the incisive papilla of the upper cast or model 92 to the lines 162 and centered on median line 164 and marked by pencil or otherwise. The lines 162 preferably are spaced metrically and preferably at 1 to 4 mm spacing, most preferably 2 mm spacing. The mark then is moved forwardly about 4 or 6 mm to determine the location for the front anterior surface of the central teeth 16 of the upper set of teeth 10. With the set of teeth held firmly in the latter position, such as shown in FIG. 37, attaching material 168, or other material referred to hereinafter, is applied between the set of teeth and the upper cast or model 92 to connect them together for further procedure.

Further to assist in such positioning of the full arch set of teeth 10 upon the surface 152 of table 114, an adjustable positioning member 166, shown in exemplary manner in FIGS. 17 and 18, may be employed with respect to the gradient lines 162 to have the foremost anterior portion of the full arch set of teeth 10 disposed against member 166 and thereby prevent movement of the teeth especially along the median line 164, for example, and thereby accurately position the teeth for applying removable attaching material 168, such as soft sticky wax, between the teeth and the upper cast 92 upon which, in accordance with usual procedure, a usually thin configuration of baseplate material, such as wax and/or plastic, or mixtures thereof, of conventional type, has been shaped to conform to the gum surface of the cast but is readily removable therefrom and to which the attaching material 168 readily adheres between the gingival portions of the full arch set of teeth 10 and the baseplate, which is not shown in detail but is of conventional type as aforesaid.

Initially, small lumps of the attaching material 168 may be used as described and ultimately, additional wax material is aesthetically shaped upon the baseplate material on the gum portion of the cast 92, in order to provide desirable contour surfaces extending upward from the teeth and resembling natural gums in the finished denture to be formed from the process being described.

Figure 38:
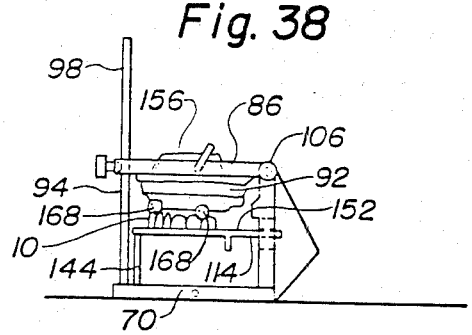
Figure 39:
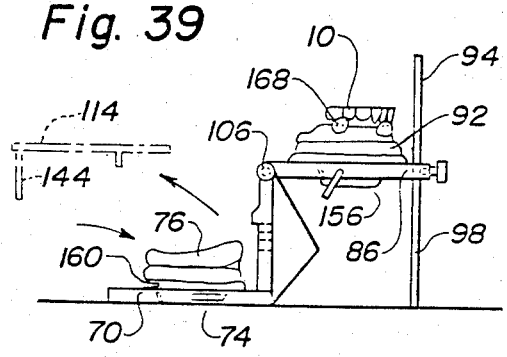
Figure 40:
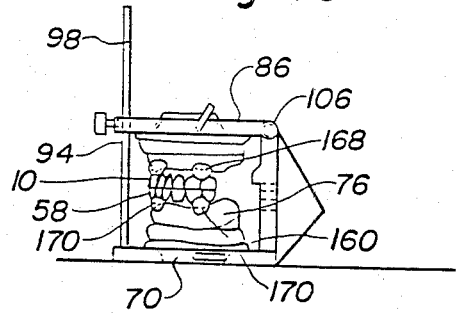

Following the steps shown in FIG. 38, and referring to FIG. 39, it will be seen that the next step comprises pivoting the upper bow 86 to the position shown in FIG. 39, followed by removing the mounting table 114 and replacing the lower cast 76 and its attaching material to the base 70, whereupon the upper bow 86 is returned to the operative position above base 70. When the lower cast 76 is in the position shown with respect to base 70 in FIG. 40, the full arch set of lower teeth 58 is placed closely in occlusion relative to the full arch set of upper teeth 10 so that they are in the proper relationship, such as shown in exemplary manner in FIG. 7, for example, whereupon the lower set of teeth 58 is at least temporarily attached to the sheet-like baseplate material previously conformed to the lower cast 76 by means of additional lumps of removable attaching material 170, or otherwise, in order to stabilize the set of lower teeth 58 with respect to the cast 76. Thereafter, as described above in regard to the upper set of teeth 10, an aesthetic application of additional wax or similar material is added to the teeth and baseplate material to resemble natural gums, whereby the lower set of teeth and baseplate on the lower denture 76 are finalized as to shape to resemble natural gums. Preferably, at this stage of the process, the radial fingers 28 of the strut means are severed from the full arch sets of the teeth, just prior to the finishing the final contouring of the wax.

After the upper and lower sets of full arch artificial teeth have been secured respectively to the baseplates upon the casts or models, both of the baseplate configurations with the artificial sets of teeth attached thereto may be removed and fitted to the patient's gums for a try-in, and if necessary, desirable adjustments may be made.

In the foregoing, reference has been made to the adjustable positioning member 166, shown in FIGS. 17 and 18. An exemplary type thereof is shown therein and may be made of metal or plastic and has a curved upright flange which abuts the forward anterior portion of the upper full arch set of teeth 10, especially to prevent forward movement thereof while attaching the same to the baseplate on the gum portion of upper cast or model 92, as can be visualized from FIGS. 37 and 38, especially. The member 166 is slotted to receive a thumb screw 161 which is threaded into a hole in table 114 and after adjustment of the curved portion relative to the indicating lines 162, the screw is tightened to secure the desired position of the member upon table 114.

After the finishing wax has been added between the respective sets of full arch teeth and the respective baseplates attached thereto so that the surface of the waxed-up products resemble the natural gums and teeth desired to be reproduced, the connected sets of teeth and baseplates are removed with the casts or models to which they are removably attached and then are processed in a conventional manner to produce the finished dentures comprising the full arch sets of artificial teeth integrally connected to conventional denture base material which is inserted into the molding cavities formed by the conventional processing methods normally employed for such purposes.

Figure 42:
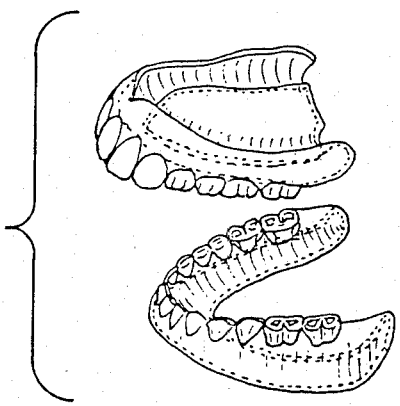
FIG. 42 is a perspective view of an exemplary set of artificial upper and lower dentures in which full arch sets of the teeth of the present invention are included.

Such conventional methods include investing the waxed-up teeth and baseplates and the upper and lower casts or models in so-called dental stone or similar material mounted in flasks of well-known type, followed by boiling out the removable material of wax or otherwise while leaving the artificial teeth, and especially the occlusal and incisal portions thereof embedded in the dental stone, thereby forming the cavity of the desired shape of the denture base to be attached to the teeth. Viscous denture base material then is placed by conventional apparatus and means into such cavity for bonding to the ridgelap surfaces of the posterior and anterior teeth and overlapping of some of the gingival surfaces of said teeth, as well as a certain amount extending at least partially into the interproximal areas 56 between adjacent teeth and clearly illustrated in FIGS. 6–8, all resulting in the formation of imitation gums contoured to resemble natural gums and attachable to the gum portions of the upper and lower jaws of the patient and retained thereagainst by suction and/or gravity, particularly in regard to the lower denture. See Fig. 42 for an exemplary illustration of such dentures.

The completed dentures are removed from the dental stone comprising the molds into which the denture base material is injected, and after suitable polishing of conventional type, the completed dentures are ready for try-ins and actual use.

Figure 41:
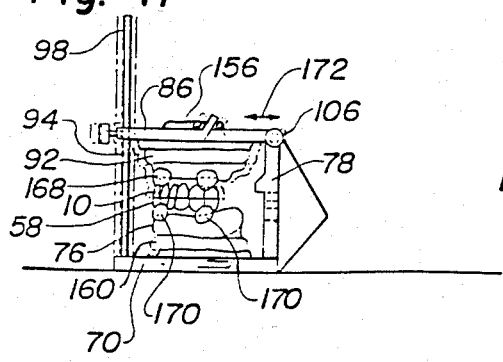

Lastly, referring to FIG. 41, when the finished dentures are completed, it is sometimes found that a limited amount of milling between the upper and lower sets of teeth is desirable in order that the incisal and occlusal surfaces thereof may suitably occlude and thus dispose the teeth and especially the occlusal and incisal surfaces thereof as shown in FIG. 7, for example, along a common occlusal plane 60. To accomplish this in accordance with the present invention, the knobs 106 of the thumb screws 104 are reversely screwed to back off the screws sufficiently to disengage the pivot extensions 108 from the central sockets 112 to an extent such as shown in phantom in FIG. 13, whereupon the pivot extensions 108 are disposed entirely within the short recesses 110 and thereby permit limited lateral movement of the upper bow with respect to the upper ends of the support members 78, as well as the base 70, and thus permit milling between the incisal and occlusal surfaces of the sets of teeth 10 and 58 to a desired extent, such movement being indicated in exemplary manner by the direction arrows 172 in FIG. 41.

Referring to FIG. 24, an exemplary substitute support 174 is shown for use upon one type of a conventional articulator in the event it is not desired to employ the articulator of the present invention and the mounting table 114 thereof. The support 174 has a planar support surface 176 and a mounting bar 178 for positioning hamular notches of the upper casts. Vertically adjustable base members 180 at opposite sides permit adjustment of surface 176 relative to the lower bow or base of such conventional articulator.

In FIG. 25, another attachment 182 is shown for use with another well-known type of articulator and is provided with a mounting bar 184 to be engaged by hamular notches of an upper dental cast.

From the foregoing, it will be seen that the above-described mechanical elements and the full arch sets of upper and lower artificial teeth of this invention result in producing desirable and highly acceptable artificial dentures with a minimum of operational steps and especially in the saving of time over that required to individually mount artificial teeth in wax in accordance with normal procedures and especially including interdigitation thereof, when necessary. Further, by utilizing preformed full arch sets of upper and lower artificial teeth, mismounting of the teeth and otherwise possibly misaligning the same is avoided, compared to the possibility of mismounting and misaligning that can occur when utilizing individual artificial teeth in the preparation of dentures.

The foregoing description has referred to the preparation of the arrangement of conventional, removable wax and baseplate material and the sets of full arch teeth attached thereto being processed into finished dentures by conventional techniques such as investing the waxed models and full arch teeth in dental "stone" and "boiling out" the removable wax and baseplate material to form a cavity into which conventional denture base material is inserted for attachment to the teeth which are partially embedded in the dental "stone." The present invention is not to be restricted to the above-described techniques, however, in that further improvements also are included in the invention which include the use of certain compositions comprising manually or mechanically applicable, actinic light-curable baseplate and denture base material in lieu of removable wax and conventional baseplate materials described above. These compositions may be quickly cured, thereby further to shorten the time required to form finished dentures in accordance with the following description.

One example of a composition that is moldable to a denture base form and is hardenable and cured by exposure to visible light was prepared from the following ingredients in the manner described hereinbelow:

| PERCENT BY WEIGHT OF TOTAL COMPOSITION | |
|---|---|
| 39.44 | Urethane dimethacrylate (Reaction product of hydroxyethyl methacrylate and 2,2,4-trimethylhexyl-1,6-diisocyanate) |
| 2.57 | 1,6-Hexanediol dimethacrylate (HDDMA) |
| 0.13 | Camphoroquinone (CQ) |
| 0.59 | DMAEMA-MAA salt prepared as in Example 2 |
| 42.10 | poly (methyl methacrylate-co-ethylene dimethacrylate 99.8:0.2) a polymer supplied by L. D. Caulk Company (Polymer is in substantially spherical beads the shape resulting from its suspension polymerization. At least 50% by weight of the beads have average diameters of less than 50 microns. The polymer was prepared from methyl methacrylate and ethylene dimethacrylate by suspension polymerization*). |
| 0.07 | red acetate fibers |
| 0.03 | pigments |
| 15.07 | fumed silica inorganic filler (Aerosil R972 a product of Degussa) |

*The polymer was prepared according to the teaching of U.S. Serial No. 318,356, filed November 5, 1981, which was a Continuation of U.S. Serial No. 008,507, filed February 1, 1977.

First CQ was dissolved in HDDMA and then mixed with the amine salt and urethane dimethacrylate. The resulting liquid solution was charged to a double planetary mixer heated to 45° C. and mixed under 20 mm Hg pressure. Next the polymer with the pigments and fibers previously blended in a V-Cone Blender was added and mixed under 20 mm pressure. The temperature was increased to 55° C. and the fumed silica was added in three increments of about equal size and mixed under 130 mm pressure each time. This produced a visible light curable (VLC) putty-paste.

By putty it is meant a viscous material that can be deformed mechanically (manually) and will at least temporarily hold the shape into which it has been deformed or molded.

The initial setup of the upper and lower stone models and determination of the relative position of the upper full arch set of teeth in an acticulator was the same as previously described and illustrated with respect to FIGS. 30 through 37. In this way, the dental models are precisely positioned in space in a manner allowing their removal and return to precisely the same position. However, from that stage forward the process did differ in the manner now to be described.

The VLC putty was then treated to remove excess entrapped air by placing the putty in a canister and subjecting it to a vacuum of 120 mm mercury and then the vacuum was released and the putty was subjected to pressure in a hydraulic press. The putty was then extruded through Deldren Dies using a ram extruder into a sheet having a size of 0.909 inch ×2⅜ inches and a rod having a diameter of 0.25 inch. The dental model was removed from the aforesaid precise position by opening the articulator to the position shown in FIG. 36. The molding surface of the dental model was provided with a coat of a release or separator system.

The separator system was a two part system:

(1) The first part of the system functioned as the gypsum mold or model sealer. This first part was prepared from the following ingredients:

| | |
|---|---|
| 0.68% | Hydroxyethyl cellulose (Natrosol 250 HR, Hercules, Inc.) |
| 97.82 | Water |
| 0.30 | Nonylphenyl ethoxylate surfactant (Makon 10, Stepan Chemical Company) |
| 0.20 | 0.1% FD & C Blue #1 Dye in water |
| 1.00 | Preservative (Glydant, Glyco, Inc.) |

The above ingredients were mixed together at ambient conditions and the resulting solution was a clear, blue colored solution with a viscosity of 354 centipoises at 22° C. (Brookfield Synchro-lectric Viscometer, model RVT, #2 Spindle, 100 rpm). This sealer was brushed over the entire gypsum model surface. The solution dried very quickly leaving an almost invisible film on the surface. The model was removed from the articulator for application of the sealer and then reset in the articulator.

(2) Then, the second part of the separator system was brushed over the coated surface, covering ONLY the areas to be in contact with VLC Denture Resin. The wet model was then dried under a hair dryer for five minutes. This second part of the separator system functioned as a surface cure promoter and was prepared from the following ingredients:

| | |
|---|---|
| 41.00% | Polyvinyl pyrrolidone (Plasdone K 29/32, GAF Corporation) |
| 58.23 | Water |
| 0.045 | Silicone antifoam (SAG 471, Union Carbide Corporation) |
| 0.225 | Surfactant (Makon 10, Stepan Chemical Corporation) |
| 0.50 | Sodium benzoate |

The above ingredients were mixed together at ambient temperature and pressure and the resulting solution was a very viscous clear yellow colored liquid with a viscosity of 850 centipoises at 22° C. (#2 spindle, 20 rpm).

A sheet of the previously described VLC putty, 3.5" long, was conformed to the desired shape on the upper dental model by pressing it into shape by hand using the techniques employed in conventional denture baseplate shaping with wax. The sheet was thereby formed or molded into a denture baseplate for the upper denture.

The baseplate was removed from the articulator and trimmed and then hardened and cured for two minutes on a turntable rotating under four 150 watt quartz-halogen lamps with a 400–500 nm band-pass filter. The turntable was in the denture curing apparatus of U.S. Ser. No. 492,284, filed May 6, 1983, which is assigned to the same assignee as the present patent application, and this is the preferred apparatus although any arrangement providing a good cure can be used and those skilled in the art can provide adequate cures in other manners. The light flux varied from 100–130 mw/cm$^2$ on the surface of the baseplate in the procedure carried out.

A full arch set of upper teeth was prepared for attachment to the upper denture baseplate by first roughening the ridgelap portion with a dental bur to assure the very best bond and then coating the ridgelap with a bonding agent to further assure an excellent bond. The bonding agent was prepared from the following ingredients:

| | |
|---|---|
| QM 657 (Rohm & Haas) | 30.00 g |
| Methyl Methacrylate | 30.00 g |
| Acrylic Acid | 6.00 g |
| 1,6-Hexanediol Dimethacrylate | 10.00 g |
| Dimethylaminoneopentyl Acrylate-Methacrylic Acid (DMANPA MAA) | 1.56 g |
| Camphoroquinone (CQ) | 0.30 g |
| Uvithane 782 (Morton-Thiokol) | 63.00 g |

The ingredients were mixed in an amber bottle at ambient conditions and then heated at 60° C. until comletely homogeneous.

The VLC Tooth Bonding Agent was brushed on the area of the teeth to be bonded and allowed to stand for two minutes. Then, the VLC Tooth Bonding Agent was light cured on the teeth by two minutes exposure, in the manner described for curing the VLC denture baseplate composition.

The reason the bonding agent is important as described is that the full arch set of teeth is made from the currently preferred polymer composition as taught in U.S. Ser. No. 318,351 filed Nov. 5, 1981 which was a continuation of U.S. Ser. No. 137,642 filed April 7, 1980, (now abandoned) which was a division of U.S. Ser. No. 008,507 filed Feb. 1, 1979 now abandoned, all of which are assigned to the assignee of the present application and the contents of which are incorporated in this application by reference. The teeth were thus comprised of acrylic plastic and without the use of mechanical locking means, a good chemical bond is preferred to assure a permanent securement of the teeth to the denture baseplate.

The full arch set of upper teeth was placed in position adjacent to the denture baseplate in a measured precise position measured in relation to the dental model of the upper jaw prior to the forming of the denture baseplate thereon. The position simulates a functional and aesthetic alignment of the full arch set of teeth relative to the denture baseplate. This was done by using the guiding indicia on the occlusion table 114 as described with respect to FIG. 37 earlier.

The upper dental model was then reinstalled in the articulator with the upper dental baseplate in position on it with the release coat between the denture baseplate and the model. The rod-shaped VLC putty was used as a tacking putty to initially secure the denture baseplate and teeth together. The tacking quantity of putty was initially applied to the denture baseplate in the rod shape around the ridge of the baseplate and curved around in the general configuration of the full arch set of teeth. The tacking quantity of putty is such that it will later be covered up and thus need not in itself offer a fully aesthetic appearance when placed, although it is preferable to and was in fact initially shaped by hand and flattened out against the denture baseplate where it contacts or engages the baseplate.

With the full arch set of teeth in their adjacent position as previously described, the portion of the articulator mounting the dental model having the shaped denture baseplate engaged thereon was hingedly closed as previously described with respect to FIG. 38. The tacking quantity of putty was trapped between the closing baseplate and the teeth. The teeth were thereby engaged with the tacking putty.

The dental baseplate will be understood to have been engaged with the full arch set of teeth with the teeth maintained in their precise measured position when the model was returned to its previously established precise position. The teeth were maintained in position by being held by hand against adjustable positioning member 166.

The tacking putty was then hardened by actinic visible light to rigidly attach and secure the full arch set of teeth to the denture baseplate providing the positioning of the full arch set of teeth for receipt of the gum simulating putty which corresponds to the previously referred to adjacent position. This hardening was by curing through the engagement of the putty with visible actinic light for two minutes in the manner previously described respecting the curing of the upper denture baseplate. In this manner the full arch set of teeth is positioned.

Next the facial and lingual aspects of the denture were finished with additional rod putty. To do this the upper jaw model was again secured to the upper articulator bow member 86 via the securing pin 90 and the articulator was opened and turned around and tipped back on its rear edge stand surface 100 for ease of working. The putty, which was of the same visible light curable composition as that used for the baseplate and the tacking putty, was molded about the teeth at their gingival ends to simulate gum tissue. The gum simulating application of putty was by hand using instruments of the type commonly employed for shaping wax to simulate gum tissue in a dental lab. The material worked well using standard techniques. Material was also added to the back of the full arch set of teeth to merge the gingival ends of the teeth with the denture baseplate more aesthetically and to provide a better feel for the denture wearer.

Thereafter the upper jaw model with the upper denture attached was removed from the articulator by removal of securing pin 90 and an oxygen barrier layer of the composition of surface cure promoter portion of the two part separator layer previously described was applied as a top coating over the exposed surfaces of the putty of the gum simulating portions and the other portions of the denture and the denture was cured with visible light for four minutes in the manner described above. This hardened the putty molded about the teeth at their gingival ends by subjecting the putty to actinic visible light engagement.

The upper and the lower jaw models were then secured in precise position in the articulator via pins 90 and 74 respectively, with the articulator in the open position as shown in FIG. 36 but with the occlusion mounting table 114 removed as illustrated in FIG. 39. The lower jaw position was established earlier, related fixedly to the position of the upper jaw model, in the position it is to be in when the upper denture baseplate is fully closed with the full arch set of upper teeth on the occlusion table 114.

The molding surfaces of the lower jaw model were coated with the same two-part release coat system as was used on the upper model and in the same manner. A sheet of the same visible light curable polymeric composition used to make the upper denture baseplate was conformed to the desired shape on the lower jaw model over the release coat in the manner practiced with the upper denture preparation. The model with the formed denture baseplate thereon was then removed from the articulator and the polymeric composition was hardened by engaging it with visible light in the manner described respecting the upper denture baseplate. The lower model with the thus formed lower denture baseplate was then resecured in the articulator with pin 74.

The articulator was then closed, bringing the upper denture just above the lower denture baseplate. Next the lower full arch set of teeth was aligned in occlusion with the upper full arch set of teeth after the upper full arch set of teeth which have already been set in their precise position. If the lower set of teeth cannot initially be fully occluded with the upper set of teeth and aligned with the lower denture baseplate for proper mounting, necessary adjustments in accordance with usual dental prosthetic techniques are used to adjust the occluded closing in proper relation with the upper denture in its earlier established precise position. Some grinding of the ridgelaps and other adjustments may be needed to obtain proper fit. In the specific sequence of operation here being described, this was required.

The full arch set of lower teeth were of the same composition as the upper teeth and were prepared for attachment to the lower denture baseplate by roughening and applying a bonding agent in the same manner as the upper full arch set of teeth.

Next a tacking quantity of the same rod-shaped putty used with respect to the upper denture was curved around in the general configuration of the intended lower full arch set of teeth. The articulator was then swung partially closed pressing the lower full arch set of teeth into the tacking putty on the lower denture baseplate while the full arch set of teeth were held in occlusion with the upper full arch set of teeth by hand.

Thereafter, the lower model with the lower denture baseplate thereon with the teeth attached was removed and the tacking putty was hardened with visible light in the manner described respecting the upper denture construction. The tacking putty was hardened in engagement with the lower full arch set of teeth.

The lower model was then resecured in the articulator with pin 74 and the struts were removed as described respecting the upper denture. This may also be done while the model is free from the articulator. Next, the articulator was tipped back on stand surface 100 and visible light curable putty was molded about the gingival ends of the teeth in the same general manner described respecting the preparation of the upper denture.

Then the lower model with attached denture was removed from the articulator by releasing pin 74 and the exposed surfaces were coated with an oxygen barrier layer as described respecting the upper denture preparation. Then, the visible light curable composition putty around the gingival ends of the teeth simulating the gum tissue and at the back of the arch at the gingival ends was hardened with visible light as described respecting the upper dentures preparation.

As a final procedure, the lower denture still mounted on the model is returned to the articulator and the thumb screws 104 are backed out and the articulator is used to mill the occlusal surfaces to enhance better occlusion. An abrasive of the type usually used for milling of plastic artificial teeth is used and the upper bow is then moved back and forth and from side to side under hand pressure.

After the milling procedure, the upper and lower dentures were removed from their respective stone models using substantially conventional techniques which involved sectioning the stone models with a saw and pulling the pieces of the stone models away from the respective dentures. The borders of the upper and the lower dentures were then trimmed and any needed smoothing of imperfections was carried out as is conventional. Then, the entire denture surfaces were polished in conventional manner using pumice, rag wheels, and buffing compounds. The surfaces were then washed with tap water and dried with a paper towel and found to be dry, shiny, and tack free. The dentures were then clinically fitted by placing them in a patient's mouth and found to give an excellent and true fit and to have a good, aesthetic appearance and to provide good function both in mastication of food and speech.

In accordance with the principles of the invention, a full arch set of artificial teeth comprises in integral combination, a pair of similar central teeth each respectively flanked on one side by a lateral tooth, the lateral teeth each being flanked on one side by a canine tooth, and each canine tooth being flanked at one side by a set of four posterior teeth each comprising a pair of bicuspid teeth next to the canine teeth, and a pair of molar teeth extending from one end of each pair of bicuspid teeth. In some situations, it may be possible to vary the exact anatomy of the full arch set of teeth described so long as the aesthetic value of a full arch set of teeth is achieved. Of course, in this day of novelty items, variations to obtain special effects are not to be understood as departing from the true contribution of the present invention.

While the present invention has been described with the overall generic invention highlighted, it will be obvious to those skilled in the art that the species of the invention have wide application. Also, while in accordance with the present statutes, what is at present considered to be the preferred embodiment of the invention has been described, it will be obvious to those skilled in the art that numerous changes and modifications may be made therein without departing from the invention, and it is therefore aimed in the appended claims to cover all such equivalent variations as fall within the true spirit and scope of the invention.

We claim:

1. A plurality of integral artificial teeth comprising at least one anterior tooth having its labial face disposed at an angle from the vertical of about 0° to 10° sloping backward from the incisal edge for at least about 70 percent of the length of the tooth, and at least one posterior tooth having its buccal face disposed at an angle from the vertical of about 1° to about 10° sloping inward from the gingival edge for at least about 90 percent of the length of the tooth.

2. The plurality of integral teeth according to claim 1 wherein said anterior tooth is a canine tooth.

3. The plurality of integral teeth of claim 1 wherein a planar member can be laid against the said buccal face of said posterior tooth and extend from the occlusal edge to the gingival edge of said tooth and not being out of contact with said tooth by more than 10° for 90 percent of the height of said tooth.

4. The plurality of integral teeth of claim 1 wherein there are at least two juxtapositioned anterior teeth and at least two juxtapositioned posterior teeth.

* * * * *